(12) United States Patent
Qin et al.

(10) Patent No.: US 10,359,491 B2
(45) Date of Patent: Jul. 23, 2019

(54) SYSTEM AND METHOD FOR VELOCITY SELECTIVE PULSES WITH ARBITRARY SHAPE USING MRI

(71) Applicant: THE JOHNS HOPKINS UNIVERSITY, Baltimore, MD (US)

(72) Inventors: Qin Qin, Ellicott City, MD (US); Peter Van Zijl, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 211 days.

(21) Appl. No.: 15/129,960

(22) PCT Filed: Apr. 17, 2015

(86) PCT No.: PCT/US2015/026301
§ 371 (c)(1),
(2) Date: Sep. 28, 2016

(87) PCT Pub. No.: WO2015/161155
PCT Pub. Date: Oct. 22, 2015

(65) Prior Publication Data
US 2017/0176564 A1    Jun. 22, 2017

Related U.S. Application Data

(60) Provisional application No. 61/981,431, filed on Apr. 18, 2014, provisional application No. 61/991,657, filed on May 12, 2014.

(51) Int. Cl.
*G01V 3/00* (2006.01)
*G01R 33/563* (2006.01)
*A61B 5/055* (2006.01)
*G01R 33/565* (2006.01)
*A61B 5/026* (2006.01)
*A61B 5/145* (2006.01)

(52) U.S. Cl.
CPC ...... *G01R 33/56308* (2013.01); *A61B 5/0263* (2013.01); *A61B 5/055* (2013.01); *A61B 5/14542* (2013.01); *G01R 33/5635* (2013.01); *G01R 33/5659* (2013.01); *G01R 33/56518* (2013.01); *G01R 33/56563* (2013.01)

(58) Field of Classification Search
CPC ................................. G01R 33/56308
USPC ........................... 324/306, 307, 309
See application file for complete search history.

(56) References Cited

U.S. PATENT DOCUMENTS 5,278,501 A * 1/1994 Guilfoyle ........... G01R 33/4816
324/300
6,518,757 B1    2/2003 Speier
(Continued)

*Primary Examiner* — Louis M Arana
(74) *Attorney, Agent, or Firm* — John Hopkins Technology Ventures

(57) ABSTRACT

The present invention is directed to a system and method for magnetic resonance imaging including an extended Fourier transform-based velocity-selective pulse train design with a pair of refocusing pulses within each velocity encoding step and accompanying phase cycling between different velocity encoding steps. The present invention is robust to B0/B1 field inhomogeneity and eddy current effects. The utility of this technique, through a velocity-selective inversion pulse, is demonstrated in a 2D velocity-selective arterials spin labeling study, which shows a reasonable agreement in CBF quantification with the standard PCASL method.

19 Claims, 5 Drawing Sheets

(56) References Cited

U.S. PATENT DOCUMENTS

| | | |
|---|---|---|
| 2007/0083105 A1 | 4/2007 | Miyazaki et al. |
| 2008/0161678 A1* | 7/2008 | Miyazaki ............. A61B 5/0263 600/419 |
| 2010/0145184 A1* | 6/2010 | Greiser ............. A61B 5/02007 600/419 |
| 2011/0304333 A1 | 12/2011 | Rapoport |
| 2012/0283547 A1 | 11/2012 | Wong et al. |
| 2013/0184561 A1* | 7/2013 | Edelman ............. A61B 5/0263 600/413 |
| 2014/0088407 A1 | 3/2014 | Shin et al. |

* cited by examiner

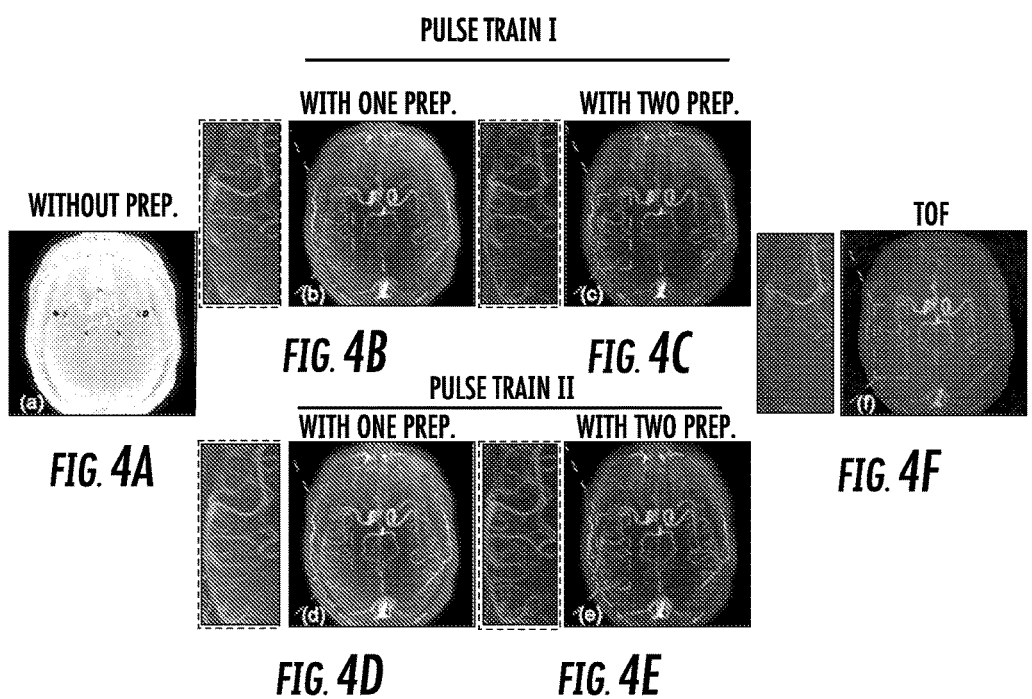

PULSE TRAIN I WITH TWO PREP.

PULSE TRAIN II WITH TWO PREP.

SYSTEM AND METHOD FOR VELOCITY SELECTIVE PULSES WITH ARBITRARY SHAPE USING MRI

CROSS-REFERENCE TO RELATED APPLICATIONS

This application is a 35 U.S.C. § 371 U.S. national entry of International Application PCT/US2015/026301, having an international filing date of Apr. 17, 2015, which claims the benefit of U.S. Provisional Patent Application Nos. 61/981,431 filed Apr. 18, 2014 and 61/991,657 filed May 12, 2014, each of which are incorporated by reference herein, in their entirety.

GOVERNMENT SUPPORT

The present invention was made with government support under grant number NIH K25 HL121192 and P41 EB015909 awarded by the National Institutes of Health. The government has certain rights in the present invention.

FIELD OF THE INVENTION

The present invention relates generally to medical imaging. More particularly, the present invention relates to a system and method for velocity selective pulses using MRI.

BACKGROUND OF THE INVENTION

Velocity-selective (VS) pulse trains can provide unique functionalities when designing pulse sequences for various Magnetic Resonance Imaging (MRI) based hemodynamic evaluation: MR angiography (MRA); blood flow (perfusion), blood volume, or transit time; oxygen extraction fraction; metabolic rate of oxygen.

Fourier-transform based VS magnetization-prepared MRA has been introduced for visualization of vessels based on the designated flow velocity and allows for a large spatial coverage. Specifically, the angiographic signal is achieved, by setting the flowing spins in the pass-band and static spins in either the inversion-band or saturation-band.

The combination of non-selective RF pulse trains with embedded velocity-encoding gradients, based on the Fourier-transform, can produce almost arbitrary velocity-selective profiles. However, the original scheme (without refocusing pulses) suffers from off-resonance effect which is manifested as excitation profile shifting along velocity. The susceptibility to B0 field inhomogeneity can be alleviated, by incorporating one composite refocusing pulse within each velocity encoding step and modifying the RF and gradient waveforms accordingly, as recently shown for peripheral MRA at 1.5 T. However, the tolerable B0 offset is limited to ±80 Hz and the sensitivity to B1 inhomogeneity remains an issue particularly at high field strength. Unfaithful B1+ scale (ratio of actual flip angle to nominal input flip angle) leads to two independent consequences: incorrect RF weighting for the excitation k-space by the hard pulse at the beginning of each velocity encoding step and thus inaccurate flip angle for either the inversion or saturation band; imperfect refocusing during each velocity encoding step and thus degraded velocity selective profile at off-resonance.

It would therefore be advantageous to provide an extended velocity-selective pulse train designed with more robust insensitivity to both B0 and B1 field inhomogeneity and eddy currents.

SUMMARY OF THE INVENTION

The foregoing needs are met by the present invention which provides a method for obtaining a magnetic resonance image or spectrum of a subject including performing a magnetic resonance imaging scan having a velocity-selective pulse train. The method also includes embedding a pair of refocusing pulses in each velocity encoding step of the velocity-selective pulse train. Additionally, the method includes applying phase cycling for the refocusing pulses in the velocity-selective pulse train.

In accordance with an aspect of the present invention, the method includes the pair of refocusing pulses taking the form of a pair of adiabatic pulses, which can be rectangular, composite, or tanh/tan adiabatic pulses. The magnetic resonance image takes the form of a neuroimage. The velocity-selective pulse train further includes velocity encoding steps. Each velocity encoding step includes a pair of refocusing pulses. The velocity-selective pulse train can further include gradient lobes. The pair of refocusing pulses are embedded among four groups of the gradient lobes. The pair of refocusing pulses constitutes a full return of a phase of a transverse magnetization.

BRIEF DESCRIPTION OF THE DRAWINGS

FIG. 1A illustrates a graphical view of a VS pulse train with a single composite refocusing pulse in each velocity encoding step (existing method). FIG. 1B illustrates a graphical view of a proposed VS pulse train I with paired composite refocusing pulses and MLEV-8 phase cycling scheme. FIG. 1B illustrates a graphical view of a proposed VS pulse train II with paired hard pulses for refocusing and MLEV-16 phase cycling scheme.

FIGS. 2A, 2D, and 2G illustrate a graphical view at representative B1+ scales of 0.8. FIGS. 2B, 2E, and 2H illustrate a graphical view of a representative B1+ scale of 1.0, and FIGS. 2C, 2F, and 2I illustrate a graphical view of a representative B1+ scale at 1.2.

FIG. 3A illustrates a graphical view of pulse train I without any phase cycling. FIG. 3B illustrates pulse train 1 with MLEV-4. FIG. 3C illustrates pulse train I with MLEV-8. FIG. 3D illustrates pulse train II without any phase cycling, and FIGS. 3E and 3F show MLEV-8, and MLEV-16, respectively. Here B1+ scale is at correct setting.

FIGS. 4A-4F display representative MIP images of results without any VS pulse trains and magnetization-prepared MRA using VS pulse train I (FIG. 4A) with one preparation (FIG. 4B) and two preparations (FIG. 4C); using VS pulse train II with one preparation (FIG. 4D) and two preparations (FIG. 4E); TOF as reference (FIG. 4F). Major cerebral arterial segments for quantitative analysis are labeled in FIG. 4A. Note the difference of depiction of small distal MCA branches in the red dashed box with the zoomed-in view between VS-MRA with one preparation (FIGS. 4B and 4D), two preparations (FIGS. 4C and 4E), and TOF (FIG. 4F), according to an embodiment of the present invention

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a system and method for magnetic resonance imaging including an extended Fourier-transform based velocity-selective pulse train design with a pair of refocusing pulses within each velocity encoding step and accompanying phase cycling between different velocity encoding steps. The present invention is robust to B0/B1 field inhomogeneity and eddy current effects. The utility of this technique is demonstrated in a VS-MRA study.

Figure 1A:
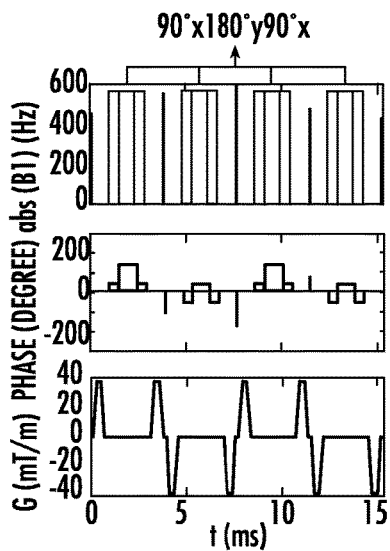
FIGS. 1A-1C illustrate graphical diagrams.
Figure 1B:
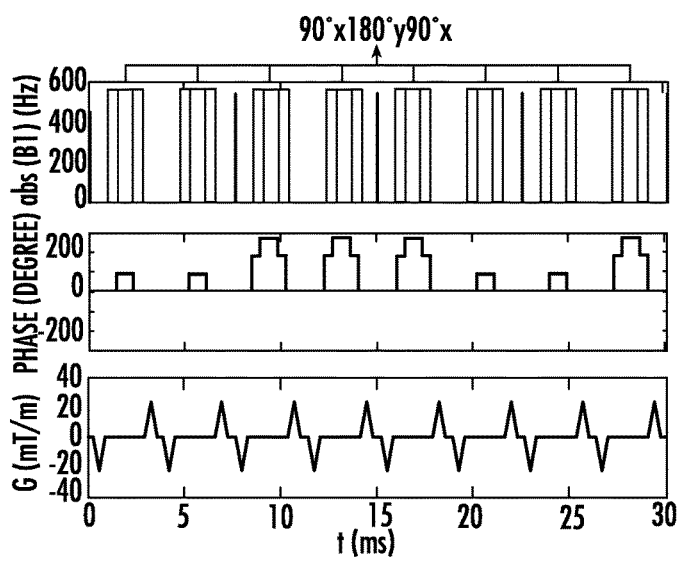
Figure 1C:
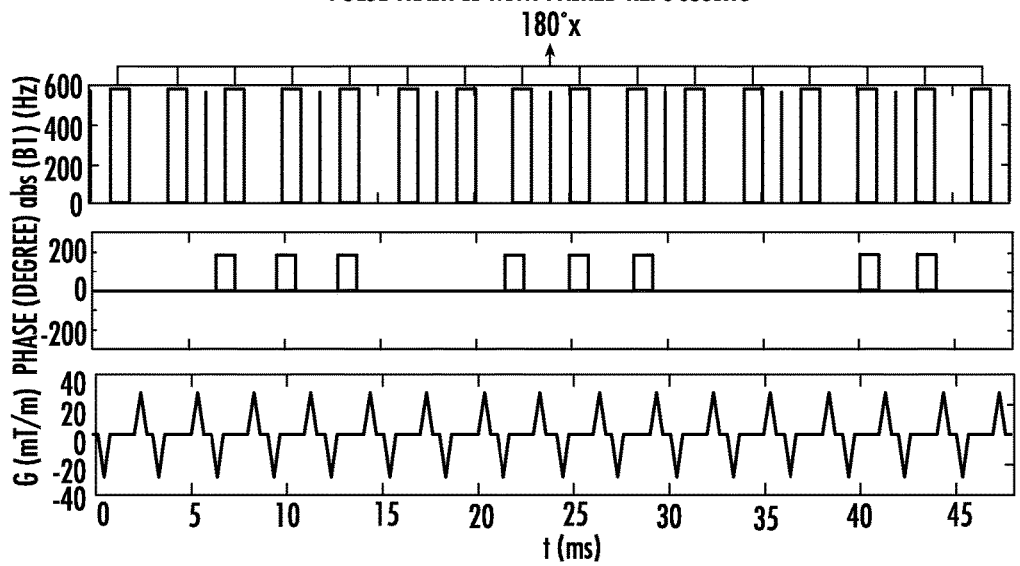

To better combat B0/B1 inhomogeneity, two sets of new VS pulse trains with paired refocusing pulses inserted for each velocity encoding step are investigated: I, 4 velocity encoding steps with 8 composite refocusing pulses ($90°_x 180°_y 90°_x$) and 5 excitation pulses (18° each) through Fourier-transform (FIG. 1B); II, 8 velocity encoding steps with 16 refocusing pulses and 9 excitation pulses (10° each) (FIG. 1C). Further improvement is realized through phase cycling of these refocusing pulses with following schemes: I, MLEV-8: [0-0-180-180-180-0-0-180]; II, MLEV-16: [0-0-180-180-180-0-0-180-180-180-0-0-0-180-180-0].

The paired refocusing pulses in each velocity encoding step of the pulse train are embedded among a group of four gradient lobes (slice direction) with alternating polarities (FIG. 1B and FIG. 1C), which leads to a flow-sensitizing gradient waveform. The refocusing pulses can take any form known to one of skill in the art including adiabatic pulses, which can be rectangular, composite, or tanh/tan adiabatic pulses.

The velocity field of view ($FOV_v$) is set to be 45 cm/s for an exemplary embodiment. FIG. 1A shows a 15 ms single refocused VS pulse train and FIG. 1B shows a 30 ms VS pulse train I with paired refocusing, both producing a saturation band within ±8 cm/s (or called cut-off velocity, $V_c$); FIG. 1C shows a 48 ms VS pulse train II with $V_c=±4$ cm/s.

Figures 2A, 2B, 2C:
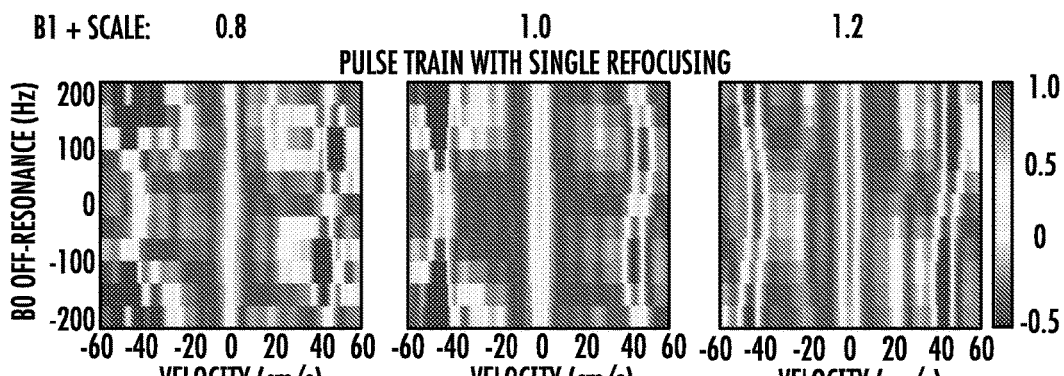
FIGS. 2A-2I illustrates graphical views of simulated Mz-velocity response of the at different B0 conditions after applying various VS pulse trains (existing pulse train with single refocusing pulses in FIGS. 2A-2C; proposed pulse trains with paired and phase cycled refocusing pulses. More particularly, pulse train I is illustrated in FIGS. 2D-2F and pulse train II is illustrated in FIGS. 2G-2I.
Figures 2D, 2E, 2F:
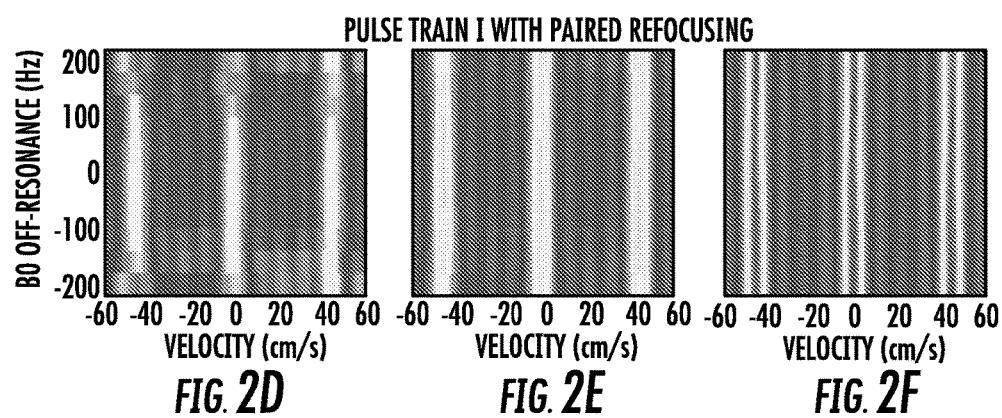
Figures 2G, 2H, 2I:
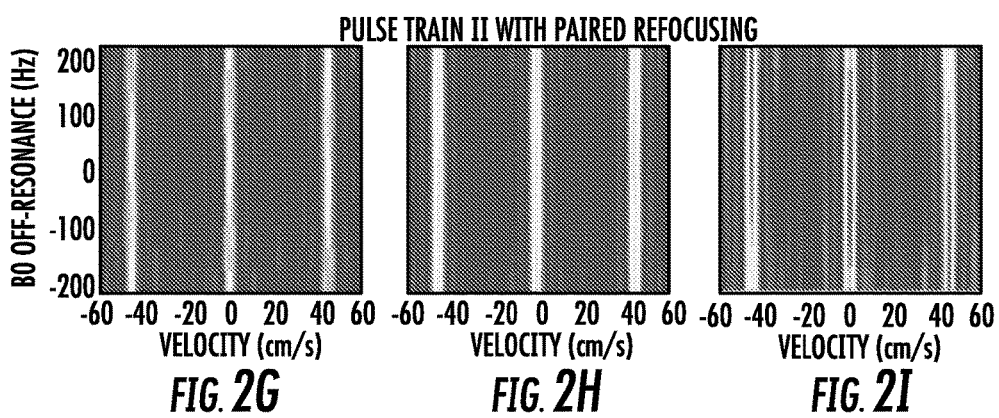

For the single refocused pulse train and our proposed pulse trains with paired and phase cycled refocusing, FIGS. 2A-2I display the Mz responses of VS pulse trains over the plane of velocity (x-axis) vs. B0 off-resonance frequency (y-axis) at three different B1+ scales (0.8 (left column), 1.0 (middle column) and 1.2 (right column)) respectively: for the single refocused pulse train (first row), significant pass-band distortion is apparent at high off-resonance, even with correct B1+ setting; for pulse trains I (second row) and II (third row), the simulated VS profiles are well maintained at different B0/B1 conditions. The Mz signal intensity within the saturation band still suffers from B1 inhomogeneity due to the hard pulses used at the beginning of each velocity encoding step. FIGS. 2A-2I illustrates graphical views of simulated Mz-velocity response of the at different B0 conditions after applying various VS pulse trains (existing pulse train with single refocusing pulses in FIGS. 2A-2C; proposed pulse trains with paired and phase cycled refocusing pulses. More particularly, pulse train I is illustrated in FIGS. 2D-2F and pulse train II is illustrated in FIGS. 2G-2I. FIGS. 2A, 2D, and 2G illustrate a graphical view at representative B1+ scales of 0.8. FIGS. 2B, 2E, and 2H illustrate a graphical view of a representative B1+ scale of 1.0, and FIGS. 2C, 2F, and 2I illustrate a graphical view of a representative B1+ scale at 1.2.

Figures 3A, 3B, 3C:
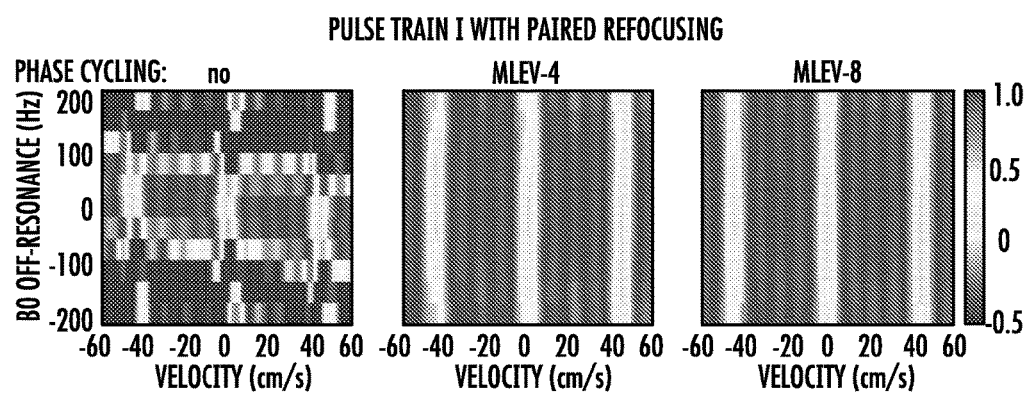
FIGS. 3A-3F illustrate graphical views of the simulated Mz-velocity responses with different phase cycling schemes.
Figures 3D, 3E, 3F:
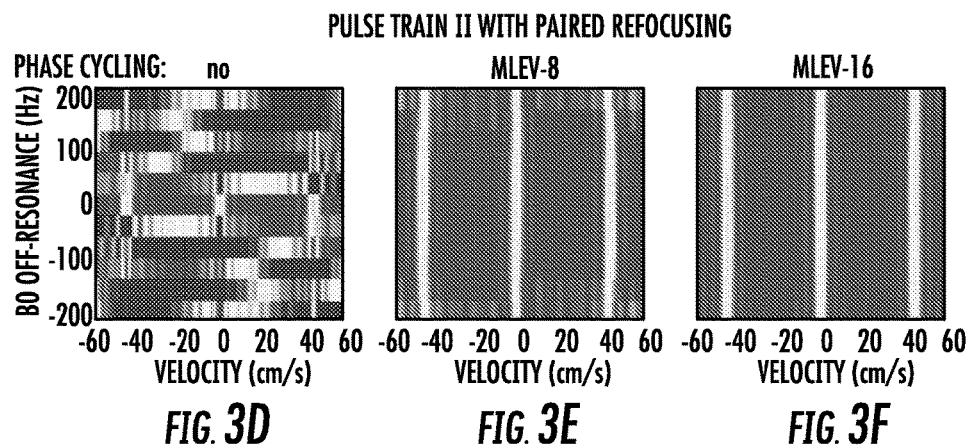

The results of pulse trains I and II without phase cycling for the refocusing pulses are shown as FIGS. 3A and 3D, respectively, which are considerably worse than those with phase cycling schemes of MLEV-4 (FIG. 3B), MLEV-8 (FIGS. 3C and 3E) and MLEV-16 (FIG. 3F) applied. It is evident that more complete phase cycling for the refocusing pulses shows more improved robustness to B0 field inhomogeneity.

Experiments were conducted on a 3 T Philips Achieva scanner. The proposed VS cerebral MRA employed turbo field echo (TFE) as the acquisition module with low-high profile ordering for the acquisition of the center of the k-space right after VS preparation pulses. A 65 mm-thick slab was acquired with a resolution of $0.7 \times 0.7 \times 1.4$ mm$^3$ and reconstructed to $0.5 \times 0.5 \times 0.7$ mm$^3$ through zero-padding. Other parameters included: readout bandwidth=193 Hz/pixel, flow-compensation gradients applied in three orthogonal orientations, TR/TE=11/6.5 ms, flip angle=15°, TFE factor=60, TFE acquisition window=650 ms, TFE shot interval=2 heart beats (or 2 sec without PPU triggering, both allowing approximately 1300 ms interval for inflow of fresh blood before VS pulse trains), SENSE factor=3 along phase-encoding direction, and total scan time=approximately 2.5 min. The exerted SAR was 33% and 60% for VS-MRA using pulse train I and II, respectively.

The utility of the VS pulse train can be much appreciated, when first compared with the acquisition without the VS module (FIG. 4A). The MIP images of VS-MRA acquired with applications of one or two preparations for VS pulse train I (FIGS. 4B-4C) and VS pulse train II (FIGS. 4D and 4E) are exhibited, respectively, with the same intensity scales. Compared to TOF-MRA (FIG. 4F), VS-MRA depicts more small distal MCA and PCA branches with slow flow at directions parallel to the axial slab. As expected, with the same velocity FOV (45 cm/s) but half the saturation band ($V_c$=4 vs. 8 cm/s), VS pulse train II (FIGS. 4D-4E) generates similar appearance for large vessels (A1 and A2 of ACA, M1 and M2 of MCA, P1 and P2 of PCA) and delineates more noticeable small vessels than VS pulse train I (FIGS. 4B-4C).

Figure 5A:
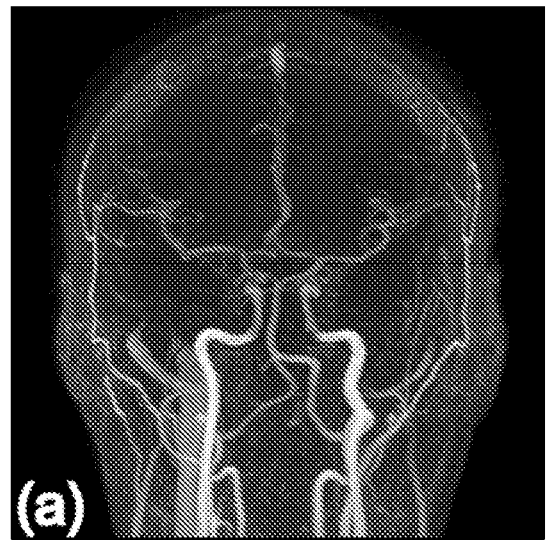
FIGS. 5A and 5B illustrate representative MIPs of VS-MRA acquired from a coronal orientation with slice-direction encoding and two preparations of VS pulse train I in FIG. 5A and II in FIG. 5B. Both head and neck arteries are labeled in FIG. 5B, according to an embodiment of the present invention.
Figure 5B:
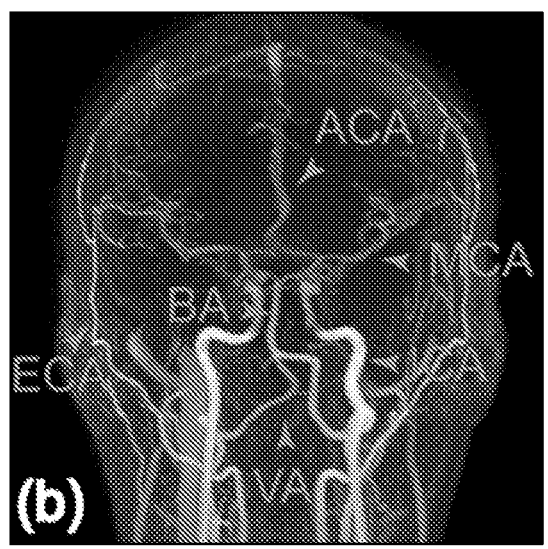

The MIPs of the two VS pulse trains (FIG. 5A: I; FIG. 5B: II) acquired with coronal orientation are exhibited. Most major arteries (ICA, ECA, VA, BA, ACA, MCA) and their small branches, especially those with slower blood flow velocity (such as VA and ACA), are better illustrated by VS pulse train II (FIG. 5B).

Velocity-selective (VS) pulse trains can provide unique functionalities when designing pulse sequences for various Magnetic Resonance Imaging (MRI) based hemodynamic evaluation: MR angiography (MRA); blood flow (perfusion), blood volume, or transit time; oxygen extraction fraction; metabolic rate of oxygen. Therefore, the present invention can be used for a number of applications including but not limited to: MR angiography (MRA); blood flow (perfusion), blood volume, or transit time; oxygen extraction fraction; metabolic rate of oxygen.

It should be noted that the pulse sequences, imaging protocols, described herein can be executed with a program (s) fixed on one or more non-transitory computer readable medium. The non-transitory computer readable medium can be loaded onto a computing device, server, imaging device processor, smartphone, tablet, phablet, or any other suitable device known to or conceivable by one of skill in the art.

It should also be noted that herein the steps of the method described can be carried out using a computer, non-transitory computer readable medium, or alternately a computing device, microprocessor, or other computer type device independent of or incorporated with an imaging or signal collection device. An independent computing device can be networked together with the imaging device either with wires or wirelessly. The computing device for executing the present invention can be a completely unique computer designed especially for the implementation of this method. Indeed, any suitable method of analysis known to or conceivable by one of skill in the art could be used. It should also be noted that while specific equations are detailed herein, variations on these equations can also be derived, and this application includes any such equation known to or conceivable by one of skill in the art.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for obtaining a magnetic resonance image or spectrum of a subject, comprising:
   performing a magnetic resonance imaging scan having a Fourier-transform based, velocity-selective pulse train comprising velocity encoding steps;
   embedding a pair of refocusing pulses in each of the velocity encoding steps of the Fourier-transform based, velocity-selective pulse train; and
   applying phase cycling for the pair of refocusing pulses in velocity encoding steps of the Fourier-transform based, velocity-selective pulse train.

2. The method of claim 1 further comprising using the pair of refocusing pulses.

3. The method of claim 1 further comprising using each one of the pair of refocusing pulses.

4. The method of claim 1 further comprising using a neuroimage as the magnetic resonance image.

5. The method of claim 1 further comprising applying phase cycling through the velocity encoding steps.

6. The method of claim 1 further comprising using the velocity-selective pulse train comprising gradient lobes.

7. The method of claim 1 further comprising embedding the pair of refocusing pulses among four groups of the gradient lobes.

8. The method of claim 1 further comprising using the pair of refocusing pulses comprising a full return of a phase of a transverse magnetization.

9. The method of claim 1 further comprising using the velocity-selective pulse train comprising an arbitrary pulse train.

10. The method of claim 1 further comprising using a non-transitory computer readable medium for the execution of the method.

11. The method of claim 1 further comprising applying the method to assessment of perfusion.

12. The method of claim 1 further comprising applying the method to angiogram.

13. A system for obtaining a magnetic resonance image of a subject, comprising:
   a magnetic resonance imaging machine configured for obtaining the magnetic resonance image;
   a non-transitory computer readable medium programmed for:
   performing a magnetic resonance imaging scan having a Fourier-transform based, velocity-selective pulse train comprising velocity encoding steps;
   embedding a pair of refocusing pulses in each of the velocity encoding steps of the Fourier-transform based, velocity-selective pulse train; and
   applying phase cycling for the pair of refocusing pulses in velocity encoding steps of the Fourier-transform based, velocity-selective pulse train.

14. The system of claim 13 further comprising using the pair of refocusing pulses.

15. The system of claim 13 further comprising using a neuroimage as the magnetic resonance image.

16. The system of claim 13 further comprising applying phase cycling through the velocity-encoding steps.

17. The system of claim 13 further comprising using the velocity-selective pulse train comprising gradient lobes.

18. The system of claim 13 further comprising determining perfusion.

19. The system of claim 13 further comprising the system being directed to angiogram.

* * * * *